United States Patent
Rezach

(10) Patent No.: US 10,335,201 B2
(45) Date of Patent: Jul. 2, 2019

(54) SPINAL IMPLANT SYSTEM AND METHODS OF USE

(71) Applicant: Warsaw Orthopedic, Inc., Warsaw, IN (US)

(72) Inventor: William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 7 days.

(21) Appl. No.: 15/415,574

(22) Filed: Jan. 25, 2017

(65) Prior Publication Data

US 2018/0206890 A1 Jul. 26, 2018

(51) Int. Cl.
| | |
|---|---|
| A61B 17/70 | (2006.01) |
| A61B 17/88 | (2006.01) |
| A61B 90/00 | (2016.01) |
| A61B 17/86 | (2006.01) |

(52) U.S. Cl.
CPC ...... *A61B 17/7032* (2013.01); *A61B 17/7035* (2013.01); *A61B 17/863* (2013.01); *A61B 2090/037* (2016.02)

(58) Field of Classification Search
CPC .............. A61B 17/7032; A61B 17/863; A61B 2017/564
USPC .......... 606/264–272, 279, 305, 328
See application file for complete search history.

(56) References Cited

U.S. PATENT DOCUMENTS

| | | | |
|---|---|---|---|
| 5,885,286 A | 3/1999 | Sherman et al. | |
| 6,565,566 B1 | 5/2003 | Wagner et al. | |
| 8,034,089 B2 | 10/2011 | Matthis et al. | |
| 8,097,025 B2 | 1/2012 | Hawkes et al. | |
| 8,167,910 B2 | 5/2012 | Nilsson | |
| 8,197,518 B2 | 6/2012 | Hammill, Sr. et al. | |
| 8,298,265 B2 | 10/2012 | Purcell et al. | |
| 8,298,275 B2 | 10/2012 | Rezach et al. | |
| 2004/0176766 A1* | 9/2004 | Shluzas | A61B 17/7032 606/65 |
| 2005/0182410 A1* | 8/2005 | Jackson | A61B 17/7032 606/278 |
| 2007/0270839 A1 | 11/2007 | Jeon et al. | |
| 2011/0093021 A1 | 4/2011 | Fanger et al. | |
| 2011/0098755 A1* | 4/2011 | Jackson | A61B 17/7008 606/305 |
| 2012/0197313 A1* | 8/2012 | Cowan | A61B 17/7037 606/305 |
| 2014/0214084 A1* | 7/2014 | Jackson | A61B 17/7037 606/270 |
| 2017/0245898 A1* | 8/2017 | May | A61B 17/7037 |

* cited by examiner

Primary Examiner — Pedro Philogene
Assistant Examiner — David C Comstock

(57) ABSTRACT

A bone fastener comprises a first member defining an implant cavity. A first part is disposed with the implant cavity and engageable with an implant. A second member is configured to penetrate tissue and includes a mating surface engageable with the first member such that the members are expandable. Implants, spinal constructs, systems, instruments and methods are disclosed.

22 Claims, 6 Drawing Sheets

SPINAL IMPLANT SYSTEM AND METHODS OF USE

TECHNICAL FIELD

The present disclosure generally relates to medical devices for the treatment of spinal disorders, and more particularly to a surgical implant system including a bone fastener and a related method.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a bone fastener is provided. The bone fastener comprises a first member defining an implant cavity. A first part is disposed with the implant cavity and engageable with an implant. A second member is configured to penetrate tissue and includes a mating surface engageable with the first member such that the members are expandable. In some embodiments, implants, spinal constructs, systems, instruments and methods are disclosed.

In one embodiment, a method of treating a spine is provided. The method comprising the steps of: reducing a spinal rod with an implant cavity of a bone fastener, the bone fastener including a first member that defines the implant cavity and a second member that is connected with tissue; and engaging the second member such that the members expand to adjust position of the implant cavity relative to the tissue.

BRIEF DESCRIPTION OF THE DRAWINGS

The present disclosure will become more readily apparent from the specific description accompanied by the following drawings, in which.

DETAILED DESCRIPTION

Figure 1:
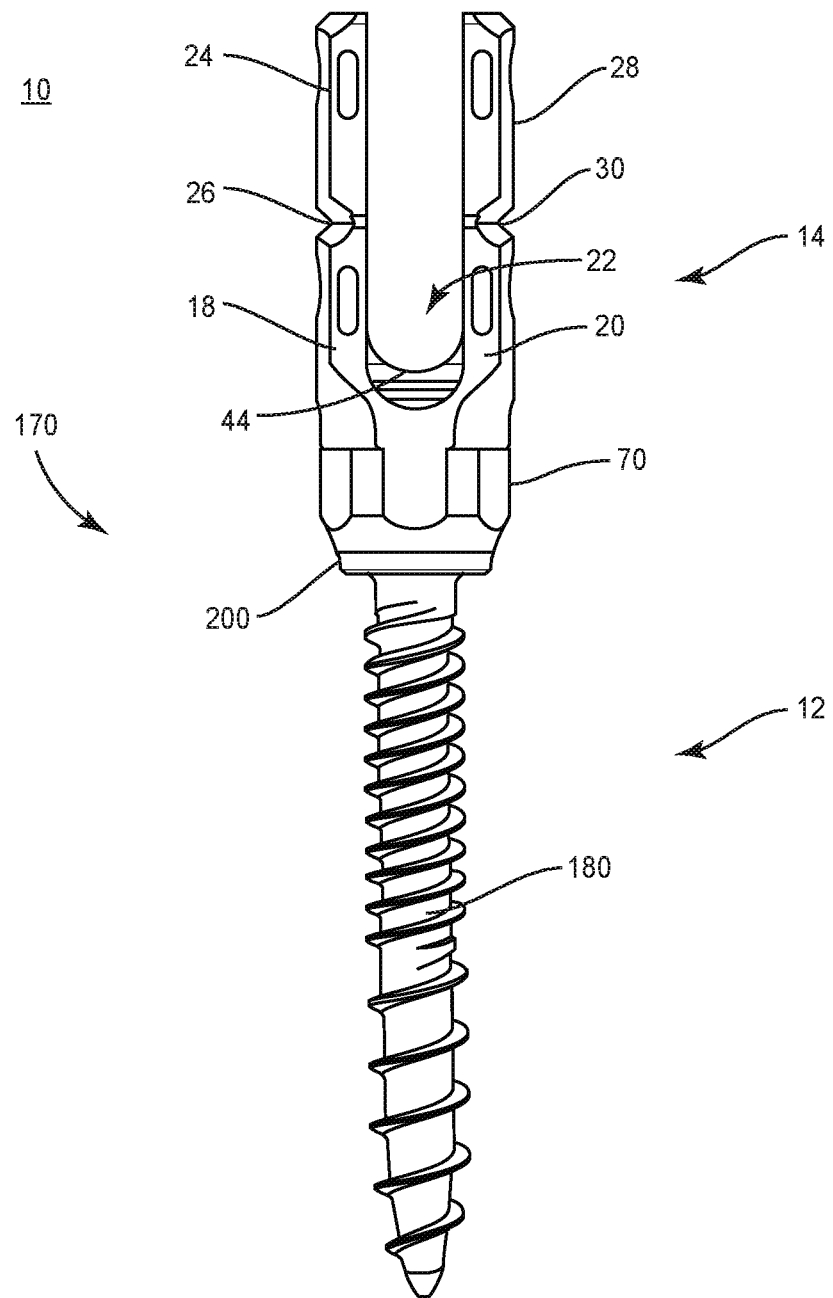
FIG. 1 is a side view of components of one embodiment of a spinal implant system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a bone fastener. In some embodiments, the spinal implant system includes an implant comprising a bone fastener, such as, for example, a pedicle bone screw. In some embodiments, the spinal implant system includes a selectively coupled pedicle screw system that allows for operating room back-table assembly of a bone fastener without use of instrumentation.

In some embodiments, the spinal implant system comprises an adjustable height pedicle screw, In some embodiments, the spinal implant system is employed with a method of treating a spine including correction and/or reduction maneuvers to apply reduction forces to fully seat a rod into a pedicle screw and/or connect a secure spinal construct with vertebrae. In some embodiments, the spinal implant system provides the flexibility to make adjustment to a spinal construct during a surgical procedure. In some embodiments, the spinal implant system allows spinal construct adjustment while avoiding the need for rod bending, loss of bone-screw interface strength and/or bone screw pull out. In some embodiments, the spinal implant system allows spinal construct adjustment to screw height to accommodate rod position relative to vertebrae.

In some embodiments, the spinal implant system comprises a modular screw system. In some embodiments, the spinal implant system comprises a modular screw system including a body that is pre-assembled with a bone screw shaft. In some embodiments, the spinal implant system comprises a modular screw system including a body that facilitates attachment of an implant receiver with a screw shaft in a robust connection. In some embodiments, the spinal implant system comprises a modular screw system including screw shaft assemblies and implant receiver/head assemblies that may be joined together during manufacturing or intra-operatively, such as, for example, during a surgical procedure in an operating room.

In some embodiments, the spinal implant system comprises a modular screw system and a surgical instrument, such as, for example, a crowfoot style offset wrench. In some embodiments, the spinal implant system is employed with a method of treating a spine including the steps of reducing a spinal rod with a bone screw of the modular screw system and adjusting bone screw height with the wrench. In some embodiments, the step of adjusting includes rotating the body with the wrench such that the body and the implant receiver separate and/or expand. In some embodiments, the body and the implant receiver include threaded connections having an equivalent pitch.

In some embodiments, the implant receiver includes a crown that is keyed to an inner surface thereof. In some embodiments, the implant receiver and the crown are fixed in rotation and relatively rotatable. In some embodiments, this configuration allows relative axial sliding of the implant receiver and the crown, and resists and/or prevents relative rotational motion. In some embodiments, the body includes a crown that is keyed to an inner surface thereof. In some embodiments, the body and the crown are fixed in rotation and relatively rotatable. In some embodiments, this configuration allows relative axial sliding of the body and the crown, and resists and/or prevents relative rotational motion.

In some embodiments, a screw shaft assembly includes at least a bone screw and a screw body. In some embodiments, the body may be assembled to the bone screw shaft using a force and/or interference fit. In some embodiments, a screw body may be assembled or retained to the bone screw shaft using one or more retaining members, such as, for example, snap rings. In some embodiments, a screw body may be assembled or retained to the bone screw shaft by displacing material of the base component, such as, for example, a swage or stake operation. In some embodiments, a screw body includes a crown and a snap ring. In some embodiments, a snap ring is engaged in a retaining groove in the body and provisionally engaged to the crown. In some embodiments, a snap ring is engaged to a part, such as, for example, a sleeve that maintains the snap ring centered. In some embodiments, the present system is employed with a method of assembly such that during assembly the screw base drives and/or translates the crown or a sleeve upwards to force the snap ring to expand and disengage the crown or sleeve. In some embodiments, the method includes the step of engaging the screw shaft assembly to create a permanent assembly of a bone fastener.

In some embodiments, the spinal implant system comprises a modular system that includes a head assembly having a tulip and a crown. In some embodiments, the spinal implant system comprises a modular system that includes a screw shaft assembly having an indexing feature. In some embodiments, the screw shaft assembly includes a shaft having a head with flats for engagement to the indexing feature. In some embodiments, the screw shaft assembly includes a screw base that is rotatable relative to an implant receiver in a range of 0 through 360 degrees.

In some embodiments, the present system is employed with a method of assembly including the step of initially engaging a screw shaft assembly with a head assembly such that the screw shaft assembly is disposed with a bore of the head assembly. In some embodiments, the method includes the step of expanding a snap ring such that the snap ring is expanded by the screw shaft assembly forcing a crown upwards in the assembly. In some embodiments, this configuration allows the crown to disengage from the snap ring. In some embodiments, the method includes the step of collapsing the snap ring such that as the screw shaft travels into the body, the snap ring collapses in a retaining groove and the bone fastener is permanently assembled.

In some embodiments, the spinal implant system comprises a modular system that includes a bone fastener including an array of selectively coupled members, such as bone screw shafts and receivers. In some embodiments, the spinal implant system comprises a selectively coupled bone fastener that can be assembled on a surgical table or in-situ. In some embodiments, the selectively coupled bone fastener is assembled with a force of less than 50 Newtons (N). In some embodiments, the bone fastener is selectively coupled with a non-instrumented assembly. In some embodiments, the non-instrumented assembly comprises manually engaging a screw shaft with a body. In some embodiments, the non-instrumented assembly comprises manually engaging the screw shaft in a pop-on engagement with a body. In some embodiments, a force required to manually engage a screw shaft with a body in a non-instrumented assembly is in a range of 2 to 50 N. In some embodiments, a force required to manually engage a screw shaft with a body in a non-instrumented assembly is in a range of 5 to 10 N. In some embodiments, a screw shaft is manually engaged with a body in a non-instrumented assembly, as described herein, such that removal of a body from the screw shaft requires a force and/or a pull-out strength of at least 5000 N. In some embodiments, this configuration provides manually engageable components of a bone fastener that are assembled without instrumentation, and subsequent to assembly, the assembled components have a selected pull-out strength and/or can be pulled apart, removed and/or separated with a minimum required force.

In some embodiments, the screw body assembly includes a ring disposed with a body connected with a screw shaft assembly. In some embodiments, the ring is configured to snap onto the screw shaft assembly. In some embodiments, the ring has a minimized thickness and/or height to facilitate snapping the ring onto the screw shaft assembly. In some embodiments, the force required to snap the ring onto the screw shaft assembly is in a range of 2 to 50 N. In some embodiments, the force required to snap the ring onto the screw shaft assembly is in a range of 5 to 10 N.

In some embodiments, the bone fastener is configured for assembly without the use of an instrument, such as, for example, a practitioner, surgeon and/or medical staff utilizes their hands for assembly. In some embodiments, the system requires minimal force to attach a body and a screw shaft assembly in-situ thereby reducing a pre-load on the vertebrae, such as, for example, the pedicle.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration, The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
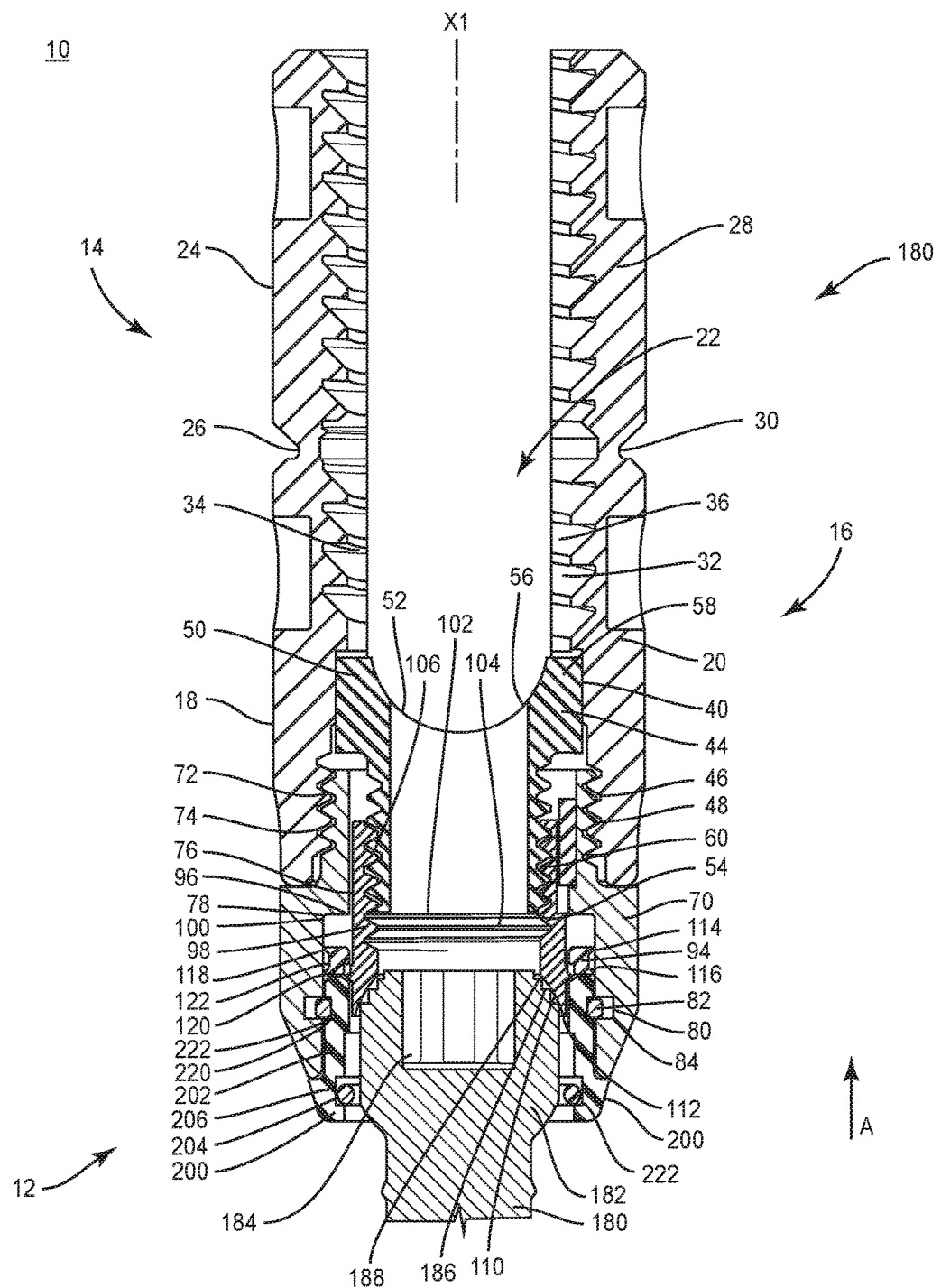
FIG. 2 is a cross section view of the components shown in FIG. 1.

The following discussion includes a description of a surgical system including a bone fastener, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-2, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials, The components of spinal implant system 10 may be monolithically formed, integrally connected or include fastening elements and/or instruments, as described herein.

Spinal implant system 10 includes a spinal implant, such as, for example, a bone fastener 170. Bone fastener 170 comprises a member, such as, for example, a screw shaft assembly 12 and a member, such as, for example, a head assembly 14. Bone fastener 170 is expandable to adjust a distance of head assembly 14 relative to tissue, for example, to selectively dispose head assembly 14 adjacent an implant or spinal construct. In some embodiments, head assembly 14 is relatively movable, for example, axially translatable relative to screw shaft assembly 12 to adjust a height of an implant cavity of head assembly 14 relative to vertebrae to accommodate position of a spinal rod for receipt thereof and/or in connection with reduction of a spinal rod with a receiver, as described herein. In some embodiments, screw shaft assembly 12 and head assembly 14 are assembled in situ or prior to implant to form bone fastener 170, as described herein.

Head assembly 14 includes a receiver 16. Receiver 16 extends along and defines an axis X1. Receiver 16 includes a pair of spaced apart arms 18, 20 that define an implant cavity 22 therebetween configured for disposal of a component of a spinal construct, such as, for example, a spinal rod 150.

Arms 18, 20 each extend parallel to axis X1. In some embodiments, arm 18 and/or arm 20 may be disposed at alternate orientations, relative to axis X1, such as, for example, transverse, perpendicular and/or other angular orientations such as acute or obtuse, coaxial and/or may be offset or staggered. Arms 18, 20 each include an arcuate outer surface extending between a pair of side surfaces. At least one of the outer surfaces and the side surfaces of arms 18, 20 have at least one recess or cavity therein configured to receive an insertion tool, compression instrument and/or instruments for inserting and tensioning bone fastener 170.

In some embodiments, arms 18, 20 are connected at proximal and distal ends thereof such that receiver 16 defines a closed spinal rod slot.

Arm 18 includes a break away tab 24 that is frangibly connected to arm 18 at a portion 26. In some embodiments, portion 26 is fabricated from a fracturing and/or frangible material such that manipulation of tab 24 relative to arm 18 can fracture and separate tab 24 from arm 18 along portion 26 at a predetermined force and/or torque limit, as described herein. In some embodiments, as force and/or torque is applied to tab 24 and resistance increases, for example, the predetermined torque and force limit is approached.

Arm 20 includes a break away tab 28 that is frangibly connected to arm 20 at a portion 30. In some embodiments, portion 30 is fabricated from a fracturing and/or frangible material such that manipulation of tab 28 relative to arm 20 can fracture and separate tab 28 from arm 20 along portion 30 at a predetermined force and/or torque limit, as described herein, In some embodiments, as force and/or torque is applied to tab 28 and resistance increases, for example, the predetermined torque and force limit is approached.

In some embodiments, tabs 28, 30 can fracture and separate at a predetermined force or torque limit, which may be in a range of approximately 2 Newton meters (N-m) to 8 Nm. In some embodiments, tabs 28, 30 and arms 18, 20 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of tabs 28, 30 from arms 18, 20.

Cavity 22 is substantially U-shaped, In some embodiments, all or only a portion of cavity 22 may have alternate cross section configurations, such as, for example, closed, V-shaped, W-shaped, oval, oblong triangular, square, polygonal, irregular, uniform, non-uniform, offset, staggered, and/or tapered. Receiver 16 includes an inner surface 32. A portion of surface 32 includes a thread form 34 located adjacent arm 18 and a thread form 36 located adjacent arm 20. Thread forms 34, 36 are each configured for engagement with a coupling member, such as, for example, a setscrew (not shown), to retain spinal rod 150 within cavity 22. In some embodiments, surface 32 may be disposed with the coupling member in alternate fixation configurations, such as, for example, friction fit, pressure fit, locking protrusion/recess, locking keyway and/or adhesive. In some embodiments, all or only a portion of surface 32 may have alternate surface configurations to enhance engagement with spinal rod 150 and/or setscrew 152, such as, for example, rough, arcuate, undulating, mesh, porous, semi-porous, dimpled and/or textured. In some embodiments, receiver 16 may include alternate configurations, such as, for example, closed, open and/or side access.

Receiver 16 includes a surface 40 configured for disposal of a part, such as, for example, a crown 44, as described herein. In some embodiments, all or only a portion of surface 40 may have alternate surface configurations, such as, for example, rough, arcuate, undulating, mesh, porous, semi-porous, dimpled and/or textured.

Receiver 16 includes a surface 46 that defines a threaded surface 48. Surface 48 is configured for a mating engagement with a threaded surface of screw shaft assembly 12, as described herein. Engagement of surface 48 with screw shaft assembly 12 facilitates relative expansion of head assembly 14 and screw shaft assembly 12, as described herein. In some embodiments, engagement of surface 48 with screw shaft assembly 12 facilitates selective axial translation of head assembly 14 relative to screw shaft assembly 12 to adjust a height of implant cavity 22 relative to vertebrae to accommodate position of a spinal rod for receipt thereof, as described herein.

Crown 44 is configured for disposal within cavity 22 and engagement with surface 40. Crown 44 includes a wall 50 having an end surface 52 and a surface 54. Surface 52 is configured to define at least a portion of cavity 22. Surface 52 is defined by an outer surface 56 that defines a curved portion of crown 44 configured for engagement with spinal rod 150. In some embodiments, all or only a portion of surface 56 may have alternate cross section configurations, such as, for example, oval, oblong triangular, square, polygonal, irregular, uniform, non-uniform, offset, staggered, and/or tapered. Surface 52 defines a receiver engagement portion, such as, for example, a flange 58 configured for mating engagement with a portion of surface 40. In some embodiments, flange 58 engages surface 40 in a keyed connection to resist and/or prevent rotation of crown 44 relative to receiver 16. In some embodiments, engagement of flange 58 and surface 40 prevents rotation of crown 44 relative to receiver 16 and allows axial translation of crown 44 relative to receiver 16.

Figure 4:
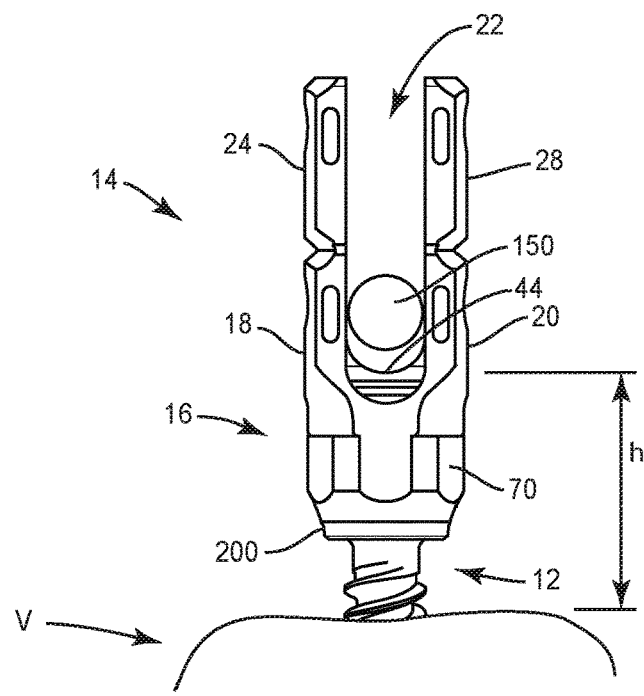
FIG. 4 is a side view of components of one embodiment of a spinal implant system in accordance with the principles of the present disclosure disposed with vertebrae.

Surface 54 includes a threaded surface 60. Surface 60 is configured for engagement with screw shaft assembly 12 for assembly of head assembly 14 with screw shaft assembly 12 and/or relative translation therebetween. Engagement of surface 60 with screw shaft assembly 12 facilitates expansion or contraction of bone fastener 170, as described herein. In some embodiments, engagement of surface 60 with screw shaft assembly 12 facilitates selective axial translation of head assembly 14 relative to screw shaft assembly 12, as described herein, Screw shaft assembly 12 includes a body 70. Body 70 includes a surface 72 that defines a threaded surface 74. Surface 74 is configured for a mating engagement with surface 48, as described herein. Engagement of surfaces 74, 48 facilitates expansion or contraction of bone fastener 170, as described herein. In some embodiments, engagement of surfaces 74, 48 facilitates selective axial translation of head assembly 14 relative to screw shaft assembly 12 to adjust a height h, as shown in FIG. 4, of an implant cavity of head assembly 14 relative to vertebrae to accommodate position of a spinal rod for receipt thereof, as described herein.

Figure 5:
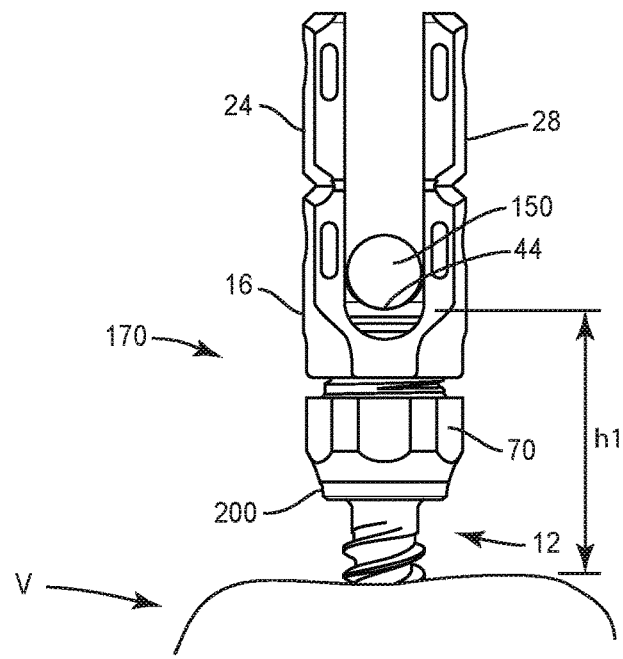
FIG. 5 is a side view of he components and vertebrae shown in FIG. 4.

In some embodiments, a surgical instrument, such as, for example, a wrench (not shown), can be engaged with head assembly 14 to rotate screw shaft assembly 12 relative to head assembly 14. Screw shaft assembly 12 is rotatable in a clockwise or counter-clockwise direction relative to head assembly 14 to expand or contract bone fastener 170. For example, rotation of receiver 16 in a counter-clockwise direction relative to body 70 causes thread surfaces 48, 74 and thread surfaces 60, 106 to simultaneously engage to selectively axially translate surface 56 from a height h to a height h1, as shown in FIGS. 4 and 5. Surface 40 resists and/or prevents crown 44 from rotating relative to receiver 16 and surface 76 resists and/or prevents a crown 98 from rotating relative to body 70, allowing for expansion of bone fastener 170 and axial translation of head assembly 14 relative to screw shaft assembly 12 along axis X1.

Body 70 includes a surface 76 that defines a cavity 78. Surface 76 defines a groove 80 configured for disposal of a band, such as, for example, a circumferential ring 82. Groove 80 includes a circumferential channel 84 that accommodates expansion of ring 82. Ring 82 includes a circumference that extends between ends of ring 82, In some embodiments, the ends define a gap. In some embodiments, the gap is sized such that the gap has a thickness that is less than the height and the width. In some embodiments, upon disposal of ring 82 with groove 80, the surface of groove 80 resists and/or prevents axial translation of ring 82 relative to axis X1.

Ring 82 is expandable and resilient between a contracted and/or capture orientation, and an expanded orientation, as described herein. Ring 82 facilitates manual assembly of body 70 with screw shaft assembly 12 in a non-instrumented assembly, as described herein. In some embodiments, ring 82 is expandable and resilient between a contracted and/or capture orientation and an expanded orientation for assembly of body 70 with screw shaft assembly 12.

In some embodiments, cavity 78 is configured for disposal of a screw shaft assembly part, which includes a sleeve 94, as described herein. In some embodiments, a lip 96 is configured as a stop surface to limit translation of sleeve 94. In some embodiments, all or only a portion of surface 76 may have alternate surface configurations, such as, for example, rough, arcuate, undulating, mesh, porous, semi-porous, dimpled and/or textured.

In some embodiments, the screw shaft assembly part includes crown 98 and sleeve 94. Crown 98 is configured for disposal within cavity 78 and engagement with surface 76. Crown 98 includes a wall 100 having a surface 102 that defines a passageway 104. Crown 44 is configured for disposal within passageway 104. Surface 102 includes threaded surface 106. Surface 106 is configured for engagement with surface 60 to facilitate axial translation of crown 44 relative to crown 98 within passageway 104. Engagement of surfaces 106, 60 facilitates expansion or contraction of bone fastener 170, as described herein. In some embodiments, crown 98 is disposed with surface 76 in a keyed connection to resist and/or prevent rotation of crown 98 relative to body 70. In some embodiments, engagement of crown 98 with surface 76 prevents rotation of crown 98 relative to body 70 and allows axial translation of crown 98 relative to body 70.

Crown 98 includes an end surface that defines an engagement portion 112 configured for engagement with a head 182 of a shaft 180 of screw shaft assembly 12, as described herein. In some embodiments, all or only a portion of portion 112 may have alternate cross section configurations, such as, for example, oval, oblong triangular, square, polygonal, irregular, uniform, non-uniform, offset, staggered, and/or tapered. In some embodiments, a part, as described herein, may include a crown, a sleeve and/or other component of screw shaft assembly 12.

Sleeve 94 includes a surface 114 that defines a cavity, such as, for example, a groove 116. In some embodiments, groove 116 extends about all or a portion of surface 114. Groove 116 includes a surface 118 and a surface 120. Surface 118 is disposed at an angle relative to axis X1 to define a ramp. Surface 120 is disposed at an angle relative to axis X1 to define a ramp. The ramps of surfaces 118, 120 are oriented in spaced apart relation. An intermediate surface 122 is disposed between the ramps. Surface 122 is substantially even and circumferentially disposed about sleeve 94. In some embodiments, the ramps of surfaces 118, 120 are selectively inclined to resist and/or prevent displacement of ring 82 from channel 84 to provisionally assemble body 70 with screw shaft assembly 12. In some embodiments, the inclination of the ramps of surfaces 118, 120 facilitate disengagement of ring 82 from groove 116 upon axial translation of sleeve 94, as described herein. In some embodiments, surfaces 118, 120 are oriented substantially perpendicular to axis X1 In some embodiments, groove 116 does not include inclined surfaces, as described above, and alternatively includes a protrusion or a lip configured to engage ring 82.

Sleeve 94 is configured for translation within surface 76 along surface 76. Sleeve 94 is configured for translation relative to crown 98 and body 70. Translation of sleeve 94 within surface 76 moves sleeve 94 between a configuration, such that ring 82 is disposed within channel 84 and groove 116 to provisionally fix body 70 with screw shaft assembly 12 and a configuration, such that ring 82 remains disposed within channel 84 of body 70 and a base 200 of screw shaft assembly 12, as described herein.

Screw shaft assembly 12 includes shaft 180 and head 182. Shaft 180 is configured to penetrate tissue, such as, for example, bone. In some embodiments, shaft 180 includes an outer surface having an external thread form. In some embodiments, the external thread form may include a single thread turn or a plurality of discrete threads. Head 182 includes a tool engaging portion 184 configured to engage a surgical tool or instrument, as described herein. In some embodiments, portion 184 includes a hexagonal cross-section to facilitate engagement with a surgical tool or instrument, as described herein. In some embodiments, portion 184 may have alternative cross-sections, such as, for example, rectangular, polygonal, hexalobe, oval, or irregular. In some embodiments, head 182 includes a surface 186 that defines a plurality of ridges 188 to improve purchase of head 182 with crown 98. Head 182 is configured for attachment with base 200, as described herein and shown in FIG. 3.

Base 200 includes a wall 202, which has a surface 204 that defines a cavity 206 configured for disposal of head 182. Surface 204 facilitates engagement of head 182 with base 200 via a pressure and/or force fit connection. In some embodiments, surface 204 facilitates a non-instrumented assembly with base 200 and head 182 via an expandable ring, similar to ring 82 described herein. In some embodiments, base 200 may be disposed with head 182 in alternate fixation configurations, such as, for example, friction fit, pressure fit, locking protrusion/recess, locking keyway and/or adhesive. In some embodiments, base 200 is configured for rotation relative to head 182. In some embodiments, base 200 is configured for rotation in range of 360 degrees relative to head 182 to facilitate positioning of shaft 180 with tissue. In some embodiments, base 200 is configured for selective rotation in range of 360 degrees relative to and about head 182 such that shaft 180 is selectively aligned for rotation in a plane relative to head assembly 14.

Wall 202 includes a surface 220 that defines a cavity, such as, for example, a groove 222. Groove 222 is configured for disposal of ring 82 to prevent displacement of ring 82 from channel 84 and to permanently fix screw shaft assembly 12 with body 70, as shown in FIG. 2. For example, base 200 is assembled with head 182 and a surface of base 200 engages sleeve 94 to release sleeve 94 from ring 82. With ring 82 expanded into channel 84, base 200 and head 182 axially translate relative to head assembly 14 within slot 90 to align groove 222 with channel 84. Alignment of groove 222 with channel 84 allows ring 82 to resiliently contract to the capture orientation, for disposal of ring 82 within groove 222 and channel 84. Ring 82 is fixed within channel 84 and groove 222. The surfaces of groove 222 resist and/or prevent disengagement of ring 82 from channel 84 and groove 222 to permanently assemble screw shaft assembly 12.

In some embodiments, body 70 is manually engageable with screw shaft assembly 12 in a non-instrumented assembly, as described herein, In some embodiments, manual engagement and/or non-instrumented assembly of body 70 and screw shaft assembly 12 includes coupling without use of separate and/or independent instrumentation engaged with screw shaft assembly 12 components to effect assembly. In some embodiments, manual engagement and/or non-instrumented assembly includes a practitioner, surgeon and/or medical staff grasping body 70 and screw shaft assembly 12 and forcibly assembling the components. In some embodiments, manual engagement and/or non-instrumented assembly includes a practitioner, surgeon and/or medical staff grasping body 70 and screw shaft assembly 12 and forcibly snap fitting the components together, as described herein. In some embodiments, manual engagement and/or non-instrumented assembly includes a practitioner, surgeon and/or medical staff grasping body 70 and screw shaft assembly 12 and forcibly pop fitting the components together and/or pop fitting body 70 onto screw shaft assembly 12, as described herein. In some embodiments, a force in a range of 2-50 N is required to manually engage body 70 and screw shaft assembly 12 and forcibly assemble the components, For example, a force in a range of 2-50 N is required to snap fit and/or pop fit assemble body 70 and screw shaft assembly 12. In some embodiments, a force in a range of 5-10 N is required to manually engage body 70 and screw shaft assembly 12 and forcibly assemble the components. For example, a force in a range of 5-10 N is required to snap fit and/or pop fit assemble body 70 and screw shaft assembly 12, In some embodiments, screw shaft assembly 12 is manually engaged with body 70 in a non-instrumented assembly, as described herein, such that removal of body 70 and screw shaft assembly 12 requires a force and/or a pull-out strength of at least 5000 N. In some embodiments, this configuration provides manually engageable components that are assembled without instrumentation, and subsequent to assembly, the assembled components have a selected pull-out strength and/or can be pulled apart, removed and/or separated with a minimum required force.

In some embodiments, spinal implant system 10 comprises a spinal implant kit, as described herein, which includes a plurality of screw shaft assemblies 12 and/or head assemblies 14. Screw shaft assembly 12 is configured for selection from the plurality of screw shaft assemblies such that screw shaft assembly 12 is connectable with an interchangeable member, such as, for example, a head assembly 14.

In assembly, operation and use, spinal implant system 10, similar to the systems and methods described herein, is employed with a surgical procedure for treating disorders of the spine, such as those described herein, as shown in FIGS. 3-8. In some embodiments, one or all of the components of spinal implant system 10 can be delivered as a pre-assembled device or can be assembled in situ.

A surgical treatment including spinal implant system 10 can be used for correction and alignment in stabilization of a treated section of vertebrae V, In an exemplary use, a medical practitioner obtains access to a surgical site including vertebrae V via a posterior surgical approach. In some embodiments, the surgical site may be accessed in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area.

An incision is made in the body of a patient and a cutting instrument (not shown) creates a surgical pathway for delivery and implantation of components of spinal implant system 10 with vertebrae V. A preparation instrument (not shown) can be employed to prepare tissue surfaces of vertebrae V, as well as for aspiration and irrigation of a surgical region.

Figure 8:
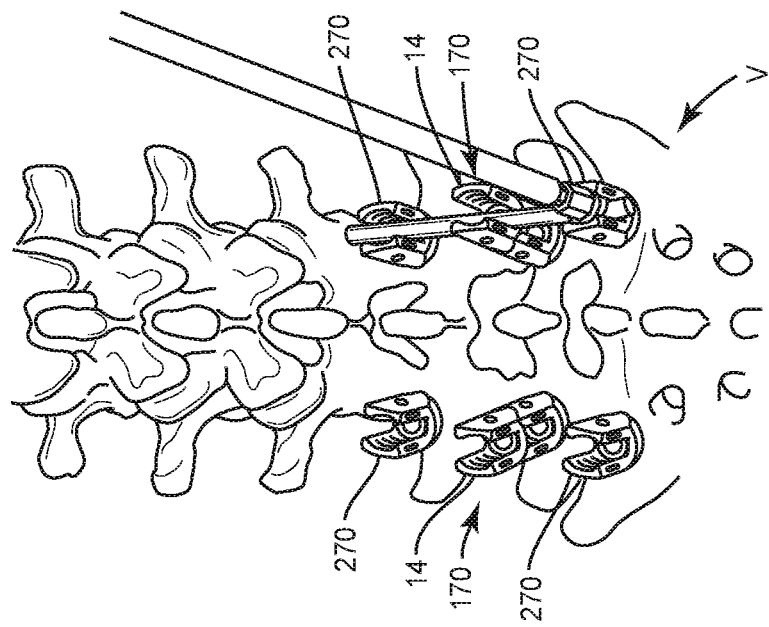
FIG. 8 is a plan view of components of one embodiment of a spinal implant system in accordance with the principles of the present disclosure disposed with vertebrae.
Figure 7:
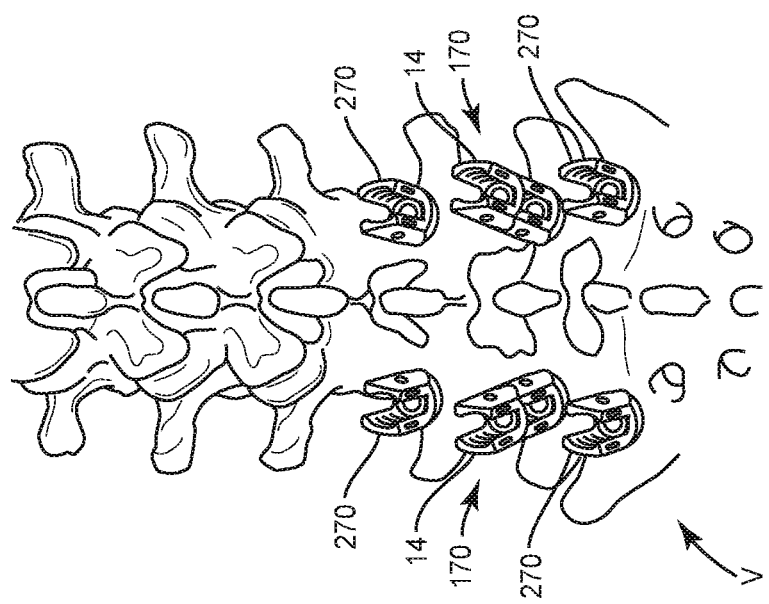
FIG. 7 is a plan view of components of one embodiment of a spinal implant system in accordance with the principles of the present disclosure disposed with vertebrae.

Spinal implant system 10 includes bone fasteners 170, as described herein, and bone screws 270, which are delivered to the surgical site for disposal with vertebrae V in connection with the surgical procedure. In some embodiments, one or more bone fasteners 170 and bone screws 270 are disposed in a serial and/or substantially linear orientation along vertebrae V, as shown in FIGS. 7 and 8. In some embodiments, one or more bone fasteners 170 and bone screws 270 are disposed with vertebrae V in alternate orientations relative to each other, such as, for example, parallel, perpendicular, adjacent, co-axial, co-planar, arcuate, offset, staggered, transverse, angular and/or relative posterior/anterior orientations and/or at alternate vertebral levels. In some embodiments, bone screws 270 include head and screw shaft assemblies, similar to assemblies 12, 14, which facilitate expansion of a bone screw 270, similar to bone fastener 170 described herein.

Figure 3:
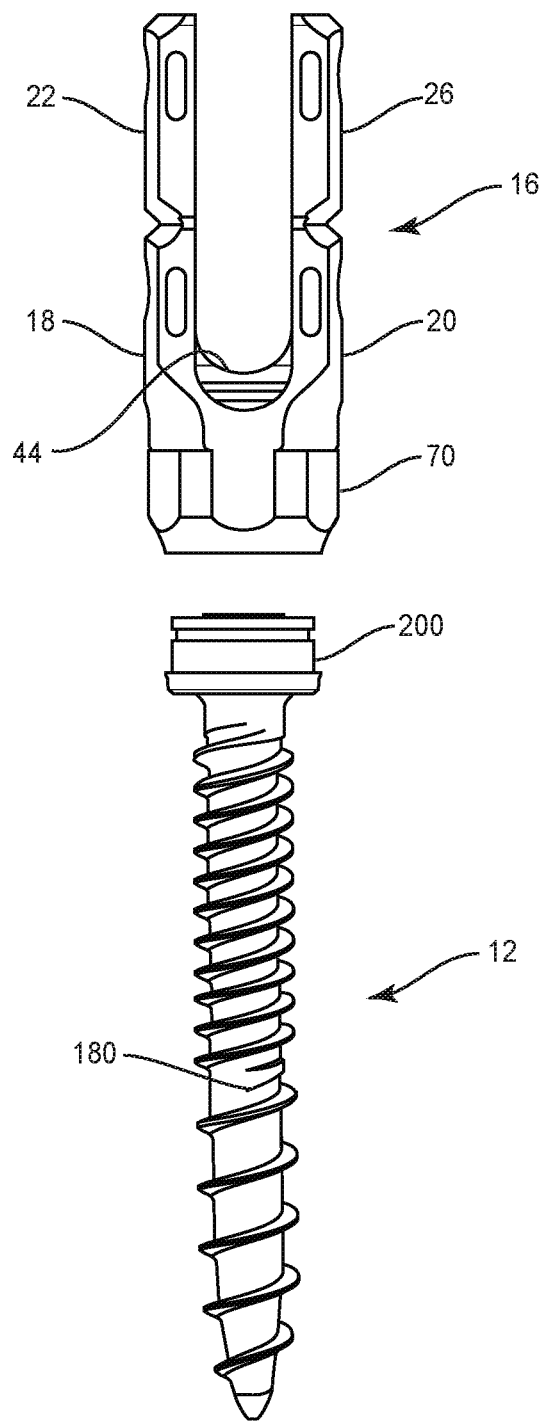
FIG. 3 is a side view of the components shown in FIG. 1 with parts separated.

Pilot holes are made in vertebrae V in a selected orientation. Bone screws 270 are aligned with the pilot holes and fastened with the tissue of vertebrae V, as shown in FIG. 7. Base 200 is engaged with head 182 for assembly of selected components of screw shaft assembly 12, as described herein. Receiver 16 is connected with body 70 by matingly engaging thread surfaces 48, 74 and thread surfaces 60, 106. Receiver 16 is threaded with body 70 for disposal in a fully contracted orientation, as shown in FIG. 3. The base 200/head 182 assembly is aligned and oriented with the receiver 16/body 70 assembly for connection therebetween, as shown in FIG. 1 and described herein. As such, head assembly 14 is assembled with screw shaft assembly 12 to form bone fastener 170, which is disposed in a contracted configuration. Bone fasteners 170 are aligned with the pilot holes and fastened with the tissue of vertebrae V, as shown in FIG. 7. In some embodiments, bone fastener 170 is assembled in a non-instrumented assembly on a back table of an operating room during a surgical procedure, as described herein. In some embodiments, bone fastener 170 is assembled in an instrumented assembly. In some embodiments, bone screw 270 is assembled, similar to bone fastener 170.

Spinal rod 150 is shaped, contoured and/or bent to a selected configuration for a selected final lordosis of vertebrae V as attached with bone screws 270 and bone fasteners 170 in connection with the surgical procedure. Spinal rod 150 is delivered to the surgical site and oriented for alignment with the implant cavities of bone screws 270 and bone fasteners 170. Reduction instruments are connected with bone screws 270 and bone fasteners 170 to reduce spinal rod 150 with the implant cavities of bone screws 270 and bone fasteners 170.

The reduction instruments manipulate bone screws 270 and vertebrae V to fully seat spinal rod 150 with bone screws 270, as shown in FIG. 8, while spinal rod 150 is not fully seated within cavity 22 of bone fastener 170, as shown in FIG. 4, for example, due to the selected shape, contour and/or bend of spinal rod 150. Coupling members (not shown) are engaged with bone screws 270 to provisionally tighten spinal rod 150.

Figure 6:
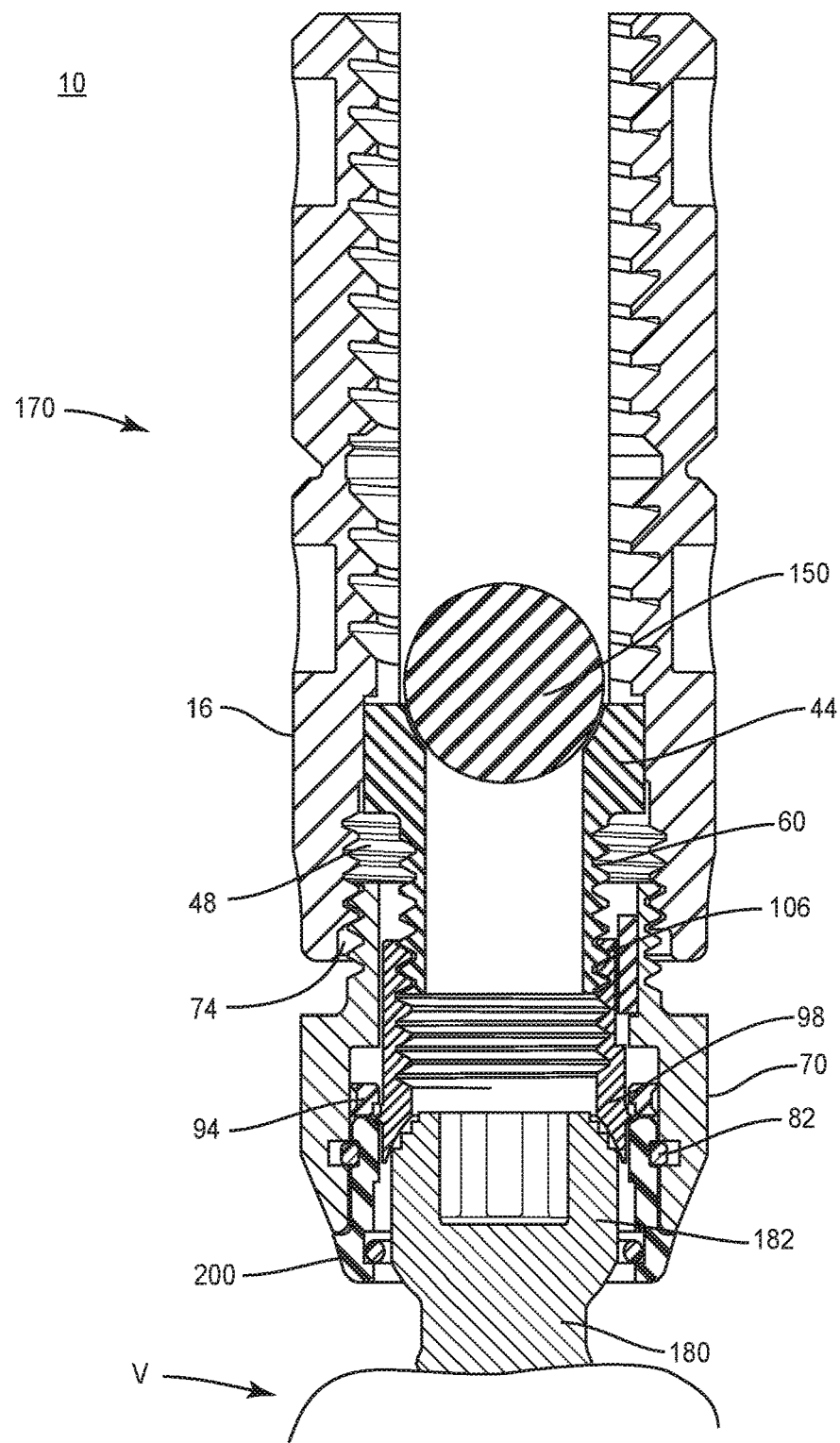
FIG. 6 is a cross section view of the components and vertebrae shown in FIG. 4.

A surgical instrument, such as, for example, a crowfoot wrench (not shown) is engaged with receiver to rotate screw shaft assembly 12 relative to head assembly 14. Bone fastener 170 is adjustable, as described herein, such that receiver 16 is rotated in a counter-clockwise direction relative to body 70 causing thread surfaces 48, 74 and thread surfaces 60, 106 to simultaneously engage, as described herein, to selectively axially translate surface 56 from a height h to a height hi relative to a tissue surface of vertebrae V, as shown in FIGS. 5, 6 and 8, Head assembly 14 axially translates relative to screw shaft assembly 12 such that bone fastener 170 expands to fully seat spinal rod 150 with cavity 22 and surface 56, and connect the spinal construct with vertebrae V. In some embodiments, this configuration allows adjustment of bone fastener 170 for reduction of spinal rod 150 therewith while avoiding the need for rod bending, loss of bone-screw interface strength and/or bone screw pull out. In some embodiments, coupling members are engaged with bone screws 270 and bone fasteners 170 to finally tighten spinal rod 150 for fixation with vertebrae V. In some embodiments, torque is applied to respective break off tabs for removal, as described herein.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

Upon completion of the procedure, the non-implanted components, surgical instruments and assemblies of spinal implant system 10 are removed and the incision is closed. In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of bone fasteners 170 or bone screws 270 described herein and/or fixation elements, which may be employed with a single vertebral level or a plurality of vertebral levels. In some embodiments, bone fasteners 170 and/or bone screws 270 may be engaged with vertebrae in various orientations, such as, for example, series, parallel, offset, staggered and/or alternate vertebral levels. In some embodiments, bone fasteners 170 and/or bone screws 270 may be configured as multi-axial screws, sagittal angulation screws, pedicle screws, mono-axial screws, uni-planar screws, fixed screws, anchors, tissue penetrating screws, conventional screws, expanding screws. In some embodiments, bone fasteners 170 and/or bone screws 270 may be employed with wedges, anchors, buttons, clips, snaps, friction fittings, compressive fittings, expanding rivets, staples, nails, adhesives, posts, connectors, fixation plates and/or post.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
   a first member defining an implant cavity;
   a first part disposed with the implant cavity and engageable with an implant; and
   a second member configured to penetrate tissue and including a mating surface engageable with the first member such that the members are expandable, the second member further including a body connected with a screw shaft, the body defining a first groove configured for disposal of a first band, the second member comprising a base defining a second groove configured for disposal of the first band to provisionally fix the base with the body, the base defining a third groove configured for disposal of a second band to facilitate engagement of the screw shaft with the base.

2. A bone fastener as recited in claim 1, wherein the second member is engageable to selectively translate the first member relative to the second member.

3. A bone fastener as recited in claim 1, wherein the members are expandable to adjust position of the implant cavity relative to the tissue.

4. A bone fastener as recited in claim 1, wherein the first member includes a threaded inner surface that mates with a threaded outer surface of the body to expand the members.

5. A bone fastener as recited in claim 1, wherein the first part includes a threaded outer surface that mates with a threaded inner surface of a crown of the second member.

6. A bone fastener as recited in claim 1, wherein the body includes a threaded outer surface that mates with a threaded inner surface of an implant receiver of the first member and the second member includes a sleeve having a threaded inner surface that mates with a threaded outer surface of the first part to expand the members.

7. A bone fastener as recited in claim 1, wherein the first member includes an implant receiver having spaced apart arms that define the implant cavity, the arms including a break off portion.

8. A bone fastener as recited in claim 1, wherein the first part is non-rotatable relative to the first member.

9. A bone fastener as recited in claim 1, wherein the body mates with an implant receiver of the first member and a second part of the second member mates with the first part to expand the members.

10. A bone fastener as recited in claim 1, wherein the body and the screw shaft are engageable in a snap-fit assembly.

11. A bone fastener as recited in claim 1, wherein the body and the screw shaft are engageable in a pop-on assembly.

12. A bone fastener as recited in claim 1, wherein the first band is expandable between a capture orientation and an expanded orientation.

13. A bone fastener as recited in claim 1, wherein the base is configured to move a second part of the second member and engages the first band to connect the body and the screw shaft.

14. A bone fastener as recited in claim 13 wherein the base is manually engageable with the body to connect the body and the screw shaft in a non-instrumented assembly.

15. A bone fastener as recited in claim 1, wherein the base includes opposite inner and outer surfaces, the outer surface defining the second groove, the inner surface defining the third groove.

16. A bone fastener as recited in claim 1, wherein the first band is disposed in the first groove and the second groove to provisionally fix the base with the body.

17. A method of treating a spine, the method comprising the steps of:
- providing a bone fastener comprising:
  - a first member defining an implant cavity,
  - a first part disposed with the implant cavity and engageable with an implant, and
  - a second member configured to penetrate tissue and including a mating surface engageable with the first member such that the members are expandable, the second member further including a body connected with a screw shaft, the body defining a first groove configured for disposal of a first band, the second member comprising a base defining a second groove configured for disposal of the first band to provisionally fix the base with the body, the base defining a third groove configured for disposal of a second band to facilitate engagement of the screw shaft with the base;
- reducing the first part with the implant cavity; and
- engaging the second member such that the members expand to adjust position of the implant cavity relative to the tissue.

18. A method as recited in claim 17 wherein the step of engaging includes rotating the second member with a surgical instrument such that the second member is selectively translated relative to the first member.

19. A method as recited in claim 17 wherein the mating surface includes a threaded outer surface that mates with a threaded inner surface of the first member to expand the members.

20. A method as recited in claim 17 further comprising the step of manually engaging the body of the second member with the second part to connect the body and the second part in a non-instrumented assembly.

21. A spinal implant system comprising:
- an implant receiver defining an implant cavity and including a crown disposable with the implant cavity;
- a spinal rod disposable within the implant cavity and engageable with the crown;
- a screw shaft being manually engageable with a body in a non-instrumented assembly, the body being threaded with the implant receiver such that the implant receiver is axially translatable relative to the body to adjust position of the implant cavity relative to tissue, the body defining a first groove configured for disposal of a first band band, a base includes an outer surface defining a second groove configured for disposal of the first band to provisionally fix the base with the body, the base defining a third groove configured for disposal of a second band to facilitate engagement of the screw shaft with the base.

22. A spinal implant system as recited in claim 21, wherein the part includes a sleeve that defines an outer groove for disposal of the band to provisionally fix the sleeve relative to the body.

* * * * *